United States Patent [19]
Perrine

[11] Patent Number: 5,216,004
[45] Date of Patent: Jun. 1, 1993

[54] METHOD FOR PREVENTING MALARIA

[75] Inventor: Susan P. Perrine, Richmond, Calif.

[73] Assignee: Children's Hospital Medical Center of North California, Oakland, Calif.

[21] Appl. No.: 582,629

[22] Filed: Sep. 13, 1990

[51] Int. Cl.⁵ ..................... A61K 31/19; A61K 31/41
[52] U.S. Cl. ..................... 514/381; 514/895
[58] Field of Search ................. 514/12, 629, 557, 381, 514/605, 578, 546, 551, 577, 895, 561

[56] References Cited

U.S. PATENT DOCUMENTS 5,025,029  6/1991  Perrine ................... 514/381

Primary Examiner—Michael G. Wityshyn
Assistant Examiner—Choon Koh
Attorney, Agent, or Firm—Heller, Ehrman, White & McAuliffe

[57] ABSTRACT

A method is provided for preventing malaria by administering to a subject an effective amount of activin, inhibin, an inhibin chain, a butyrate analog, or mixtures thereof, to inhibit the development of malarial parasites.

11 Claims, No Drawings

METHOD FOR PREVENTING MALARIA

The present invention is directed to a method for preventing malaria. In particular, the present invention is directed to a method for preventing malaria by introducing to a subject agents that increase fetal hemoglobin.

BACKGROUND OF THE INVENTION

Malaria is a group of diseases caused by hemosporidian blood parasites of the genus Plasmodium, transmitted by mosquitoes. After development in the host's liver, the parasites attack erythrocytes in the bloodstream. Development of the parasites in the erythrocytes, division and simultaneous bursting produce malarial attack.

Fetal hemoglobin inhibits the maturation of the malaria parasites, but after about four months, the human body's production of fetal hemoglobin is substantially decreased.

It is thus an object of the present invention to provide a method for preventing malaria by administering, butyrate analogs, activin or an activin-related peptide, to a subject at risk of being infected by the malaria-causing blood parasites, to increase fetal hemoglobin production.

Activin, a hormone, sometimes also referred to as erythroid differentiation factor (EDF) or follicle-stimulating hormone releasing protein (FRP), is a homodimer consisting of either two $\beta_A$ subunits of inhibin (Activin A), two $\beta_B$ subunits of inhibin (Activin B), or a subunit each of $\beta_A$ and $\beta_B$ (Activin AB). Inhibin is another hormone which, among other effects, suppresses secretion of FSH (follicle-stimulating hormone) from the pituitary gland. Inhibin is a protein consisting of $\alpha$ and $\beta_A$ subunits linked by disulfide bonds. Activin is present, in analogous forms, in mammals and have been reported, for instance, in human, porcine, and bovine follicular fluid. Porcine inhibin has been purified and sequenced from porcine follicular fluid as described in U.S. Pat. No. 4,740,587. The DNA encoding the prepro inhibin $\alpha$ and $\beta$ chains of porcine or human inhibin has been isolated, ligated into expression vectors and expressed in mammalian culture. See European Patent Application No. 222,491, published May 20, 1987. Activin A has been shown to induce hemoglobin accumulation in a human erythroleukaemic cell line and to induce the proliferation of erythroid progenitor cells in human bone marrow culture. See Yu, et al., Nature, 330, 765 (Dec. 24, 1987). The structures and isolation of activin have been reported by several groups in the literature. See Vale, et al., Nature, 321: 776 (1986); Ling, et al., Nature, 321: 779 (1986); Ito, et al., Biochem. Biophys. Res. Comm., 142, 1095 (1987); Tsuji, et al., Biotech. Bioeng., 31, 675 (1988); Shibata, et al., Biochem. Biophys. Res. Comm., 146, 187 (1987).

SUMMARY OF THE INVENTION

The present invention provides a method for treating malaria comprising the step of introducing to a subject at risk of being infected with malaria-causing blood parasites, a compound selected from the group consisting of activin, inhibin, an inhibin chain, butyrate analogs and mixtures thereof in an effective amount sufficient to eliminate development of malarial parasites.

DESCRIPTION OF THE INVENTION

In accordance with the present invention, activin, inhibin, in any of their analogous mammalian forms, or mixtures of these are introduced to the subject.

An effective amount of a butyrate analog of the formula I:

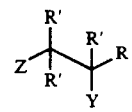

wherein R is —CO$_2$R$_1$, —SOR$_1$, —SO$_3$R$_1$, or

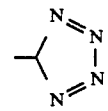

and R is NH$_2$, H, M, branched or linear alkyl 1–4 carbons or partially or perfluorinated branched or linear alkyl of 1–4 carbon atoms, and M is a cation; Z is —CH$_3$, —X, or —CX$_3$; and X is H, Cl, F, Br, I or combinations thereof; Y is H, —NH$_2$, —NH$_3^+$, —CX$_3$ or F; and R' is H or F; or mixtures of these, sufficient to inhibit development of malarial parasites may be introduced to a subject. The present invention also encompasses the use of mixtures of any two or more with the above components.

As used herein, the term "biological sample" means any cells or body fluid from a mammal that can be diagnosed, including blood erythroid progenitors.

It is also intended that variants and single chains of activin or inhibin will be utilized alone or in mixtures with each other, or with activin and/or inhibin. By the terms "activin" and "inhibin" it is meant the dimers of $\beta$ and $\beta$-chains of inhibin, prepro forms, and their prodomains, together with glycosylation and/or amino acid sequence variants thereof. The precursor may be used with or without the mature protein, and, after cleavage from the mature protein, may be non-covalently associated with the mature protein. By the term "inhibin chain" it is meant to include, but not to be limited to, the $\alpha$ and $\beta$ chains of inhibin, as well as their prepro forms and their prodomains, together with glycosylation and/or amino acid sequence variants of each chain thereof.

Generally, amino acid sequence variants will be substantially homologous with the relevant portion of the porcine or human $\alpha$ or $\beta$ chain sequences set forth in the aforementioned European Patent Application 222,491, which is incorporated herein by reference in its entirety.

Substantially homologous means that greater than about 60% of the primary amino acid sequence of the homologous polypeptide corresponds to the sequence of the porcine or human chain when aligned in order to maximize the number of amino acid residue matches between the two proteins. Alignment to maximize matches of residue includes shifting the amino and/or carboxyl terminus, introducing gaps as required and/or deleting residues present as inserts in the candidate. Typically, amino acid sequences variants will be greater than about 70% homologous with the corresponding native sequences.

Variants that are not hormonally-active fall within the scope of this invention, and include polypeptides that may or may not be substantially homologous with either a mature inhibin chain or prodomain sequence, but which are (1) immunologically cross-reactive with antibodies raised against the native counterpart or (2) capable of competing with such native counterpart polypeptides for cell surface receptor binding. Hormonally inactive variants are produced by the recombinant or organic synthetic preparation of fragments, in particular the isolated $\beta$ chains of inhibin, or by introducing amino acid sequence variations so that the molecules no longer demonstrate hormonal activity as defined above.

Immunological or receptor cross-reactivity means that the candidate polypeptide is capable of competitively inhibiting the binding of the hormonally-active analogue to its receptor and/or to polyclonal antisera raised against the hormonally-active analogue. Such antisera are prepared in conventional fashion by injecting goats or rabbits S.C. with the hormonally-active analogue or derivative in complete Freunds adjuvant, followed by booster intraperitoneal or S.C. injections in incomplete Freunds.

The variants of inhibin include the pro and/or prepro sequences of the inhibin $\alpha$ or $\beta$ chain precursors, or their immunologically or biologically active fragments, substantially free of the corresponding mature inhibin chains. The sequences for porcine and human inhibin are known, for example, as published in European Patent Application 222,491. The prepro sequence for the porcine $\alpha$ subunit precursor is the polypeptide comprised by residues 1 to about 230, while the $\beta_A$ subunit pro sequence is comprised by residues 1 to about 308. These sequences encompass prodomain sequences.

The intact isolated prepro or prodomain $\beta_A$, $\beta_B$ or $\alpha$ sequences are best synthesized in recombinant cell culture and the individual subcomponent domains are synthesized by routine methods of organic chemistry or by recombinant cell culture, for example as described in European Patent Application 222,491.

While the site for introducing a sequence variation is predetermined, it is unnecessary that the mutation per se be predetermined. For example, in order to optimize the performance of mutation at a given site, random mutagenesis may be conducted at the target codon or region and the expressed inhibin mutants screened for the optimal combination of desired activity. Techniques for making substitution mutations at predetermined sites in DNA having a known sequence are well known, for example M13 primer mutagenesis.

Mutagenesis is conducted by making amino acid insertions, usually on the order of about from 1 to 10 amino acid residues, or deletions of about from 1 to 30 residues. Substitutions, deletions, insertions or any subcombination may be combined to arrive at a final construct. Preferably, however, only substitution mutagenesis is conducted. Obviously, the mutations in the encoding DNA must not place the sequence out of reading frame and preferably will not create complementary regions that could produce secondary mRNA structure.

Covalent modifications of inhibin, activin or prodomains are included within the scope hereof and include covalent or aggregative conjugates with other chemical moieties. Covalent derivatives are prepared by linkage of functionalities to groups which are found in the inhibin amino acid side chains or at the N- or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as seryl or alanyl; and N-acyl derivatives of the amino terminal amino acid or amino-group containing residues, e.g. lysine or arginine. The acyl group is selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in crosslinking proteins to insoluble matrices through reactive side groups, e.g. m-maleimidobenzoyl-N-hydroxy succinimide ester. Preferred derivatization sites are at histidine residues.

All of these variants of activin and inhibin, as well as inhibin itself, are intended to be within the scope of the term "activin-related peptides."

In accordance with the present invention, a compound of the formula I or a mixture of two or more thereof, are introduced into the subject at risk of malarial infection. The foregoing may be administered as their non-toxic salts, such as their sodium salts, ammonium salts, potassium salts, and the like. Preferred compounds are L-$\beta$-amino-n-butyric acid, L-$\alpha$-amino-n-butyric acid, DL-$\alpha$-amino-n-butyric acid, sodium butyrate, $\beta$-chloro-D-alanine, 3-chloro-proprionicacid, 5-(2-chloroethyl)tetrazole, heptafluoro-butyric acid, monobutyrin, propanesulfinate, isobutyramide, butyramide, perfluoroisobutyric acid, arginine, heptafluorobutyric acid, isobutyric acid, similar fluorinated or branched chain analogs, and particularly arginine salts.

The method used to introduce the compound will be any convenient method normally used to introduce pharmaceuticals into the bloodstream, such as by injection, bolus, infusion, and the like. Parenteral administration may also be utilized, such as by oral administration of pharmaceutically acceptable salts of the activin, activin-related peptide and/or butyrate analog.

The exact size of an effective dose of a compound according to the method of the present invention will depend on a number of factors, including the particular recipient and the severity of the malarial condition; thus the route of administration will be ultimately at the discretion of the attendant physician.

While it is possible to utilize the compounds in vivo per se, it is preferable to present them as a pharmaceutical formulation preparation. The formulation of the present invention comprises a compound as previously described together with one or more acceptable carriers therefor and, optionally other therapeutic ingredients. The carriers must be acceptable in the sense of being compatible with other ingredients of the formulation and not deleterious to the recipient.

Activin, activin-related peptide, butyrate analog, or mixtures of these, may be administered to the subject by any suitable technique, including parenteral, sublingual, topical intrapulmonary, and intranasal administration. The specific route of administration will depend, e.g., on the type of therapy required. Examples of parenteral administration include intramuscular, subcutaneous, intravenous, intraarterial, and intraperitoneal administration.

The compositions to be used in the therapy will be formulated and dosed in a fashion consistent with good medical practice taking into account the clinical condition of the individual patient, the site of delivery of the composition, the method of administration, the scheduling of administration, and other factors known to practitioners. The "effective amount" for purposes herein is thus determined by such considerations.

As a general proposition, the total pharmaceutically effective amount of the activin, activin-related peptide, and/or butyrate analog administered parenterally per dose will be in the range of about 50 μg/kg/day to 10 mg/kg/day of patient body weight, although, as noted above, this will be subject to a great deal of therapeutic discretion. The key factor in selecting an appropriate dose is the result obtained, as measured by the subject's response, which may be measured by amelioration or elimination of the symptoms of malarial attack.

The composition herein is also suitably administered by sustained release systems. Suitable examples of sustained release compositions include semi-permeable polymer matrices in the form of shaped articles, e.g., films, or microcapsules. Sustained release matrices include polylactides (U.S. Pat. No. 3,773,919, EP 58,481), copolymers of L-glutamic acid and gamma-ethyl-L-glutamate (U. Sidman, et al., *Biopolymers*, 22, 547–556 (1983)), poly(2-hydroxyethyl methacrylate) (R. Langer, et al., *J. Biomed. Mater. Res.*, 15: 167–277 (1981), and R. Langer, *Chem. Tech.* 12:: 98–105 (1982)), ethylene vinyl acetate (R. Langer, et al., Id.) or poly-D-(−)-3-hydroxybutyric acid (EP 133,988). Sustained release compositions also include liposomally entrapped activin or inhibin or a mixture thereof. Such compositions are prepared by methods known per se: DE 3,218,121; Epstein, et al., *Proc. Natl. Acad. Sci.* U.S.A., 82: 3688–3692 (1985); Hwang, et al., *Proc. Natl. Acad. Sci.* U.S.A. 77: 4030–4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy.

For parenteral administration, the activin or activin-related peptide is formulated generally by mixing it at the desired degree of purity, in a unit dosage injectable form (solution, suspension, or emulsion) with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the activin, activin-related peptide, and/or butyrate analog uniformly and intimately with liquid carriers or finely divided solid carriers or both and then, if necessary, shaping the product into the desired formulation. Preferably the carrier is a parenteral carrier, more preferably a solution that is isotonic with the blood of the recipient. Examples of such carrier vehicles include water, saline, Ringer's solution, dextrose solution, and 5% human serum albumin. Nonaqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients. The activin is typically formulated into such vehicles at a concentration of about 10/μg/ml to 100 μg/ml at physiological pH.

Activin for use in therapeutic administration must be sterile. Sterility is readily accomplished by sterile filtration through (e.g., 0.2 micron) membranes. Activin B ordinarily will be stored in unit or multidose containers, for example, sealed ampoules or vials, as an aqueous solution, as it is highly stable to thermal and oxidative denaturation. Lyophilized formulations for reconstitution are also acceptable.

Preferred unit dosage formulations are those containing a daily dose or a unit daily subdose, or an appropriate fraction thereof.

The frequency and dosages of administration of the above compounds will depend upon infant or adult, the size and weight of the subject, the condition of the patient, and the like. Generally, injections of activin, activin-related peptide and/or butyrate analog beginning at a dosage of about 50 μg/kg–10 mg/kg; and often as low as 50 μg/kg–100 μg/kg body weight per day, particularly after onset of a malarial attack. Dosages, up to about 10 mg/kg/day may be utilized at the discretion of the physician.

What is claimed is:

1. A method for preventing malaria in a subject comprising the step of administering to said subject, a compound of the formula I:

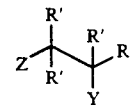

wherein: R is —CO$_2$R$_1$, —SOR$_1$, —SO$_3$R$_1$, or

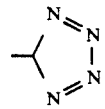

and R$_1$ is NH$_2$, H, M, branched or linear alkyl of 1–4 carbons or partially or perfluorinated branched or linear alkyl of 1–4 carbon atoms, and M is a cation; Z is —X or —CX$_3$ and X is HCl, F, Br, I or combinations thereof; Y is H, —NH$_2$, —NH$^+$$_3$, —CX$_3$ or F; and R' is H or F or a mixture thereof, in an amount sufficient to inhibit development of malarial parasites.

2. A method according to claim 1 wherein said compound comprises α-amino-n-butyric acid.

3. A method according to claim 1 wherein said compound comprises sodium butyrate.

4. A method according to claim 1 wherein said compound comprises β-chloro-D-alanine.

5. A method according to claim 1 wherein said compound comprises 3-chloro-proprionic acid.

6. A method according to claim 1 wherein said compound comprises butyramide.

7. A method according to claim 1 wherein said compound comprises salts of heptafluorobutyric acid.

8. A method according to claim 1 wherein said compound comprises α-aminopropanesulfonic acid.

9. A method according to claim 1 wherein said compound comprises sodium propanesulfinate.

10. A method according to claim 1 wherein said compound comprises isobutyramide.

11. A method according to claim 1 wherein said compound comprises monobutyrin.

* * * * *

UNITED STATES PATENT AND TRADEMARK OFFICE
CERTIFICATE OF CORRECTION

PATENT NO. : 5,216,004
DATED : June 1, 1993
INVENTOR(S) : Susan P. Perrine

It is certified that error appears in the above-indentified patent and that said Letters Patent is hereby corrected as shown below:

Column 2, line 22, change "R" to --$R_1$--

Column 6, line 44, change "HCl, to --H, Cl,--

Signed and Sealed this

Twenty-eighth Day of December, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,216,004
DATED : Jun. 1, 1993
INVENTOR(S) : Susan P. Perrine

It is certified that error appears in the above-indentified patent and that said Letters Patent is hereby corrected as shown below:

At Column 1, line 1, please insert:

--This invention was made with government support under HL-37118 awarded by the National Institutes of Health. The government has certain rights in the invention.--

Signed and Sealed this

Twenty-second Day of March, 1994

Attest:

BRUCE LEHMAN

Attesting Officer     Commissioner of Patents and Trademarks